United States Patent [19]

Kay et al.

[11] Patent Number: 4,987,153

[45] Date of Patent: Jan. 22, 1991

[54] ALKYLAMINOAMIDE COMPOUNDS

[75] Inventors: David P. Kay, Purton Swindon; Peter D. Kennewell, Okus Swindon, both of Great Britain

[73] Assignee: Roussel Uclaf, Paris, France

[21] Appl. No.: 229,922

[22] Filed: Aug. 8, 1988

Related U.S. Application Data

[62] Division of Ser. No. 883,914, Jul. 10, 1986, Pat. No. 4,782,075.

[30] Foreign Application Priority Data

Jul. 15, 1985 [FR] France ................... 85 17854

[51] Int. Cl.$^5$ ................... A61K 31/165; C07C 233/00
[52] U.S. Cl. ................... 514/620; 564/163; 564/164; 564/166
[58] Field of Search ............... 564/163, 164, 166, 620

[56] References Cited

U.S. PATENT DOCUMENTS 4,331,816  5/1982  Hadley ................... 564/164

OTHER PUBLICATIONS

Furukawa et al., "Chemical Abstracts", vol. 79, Section 31636x, Column 1 (1973).
Large et al., "Chemical Abstracts", vol. *&, Section No. 117562x, p. 570 (1977).

Primary Examiner—Robert V. Hines
Attorney, Agent, or Firm—Bierman and Muserlian

[57] ABSTRACT

Novel alkylaminoamides of the formula

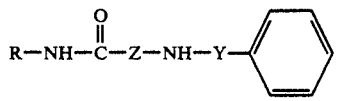

I wherein R is selected from the group consisting of (a) alkyl of 1 to 8 carbon atoms, (b) cycloalkyl of 3 to 7 carbon atoms optionally substituted with phenyl, (c) aryl of 6 to 14 carbon atoms optionally substituted with at least one member of the group consisting of halogen, —$CF_3$, alkyl of 1 to 6 carbon atoms, —$NO_2$ and cycloalkyl of 3 to 7 carbon atoms, (d) aralkyl of 7 to 14 carbon atoms and (e)

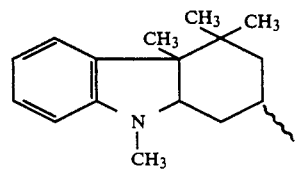

Z is —$(CH_2)_n$— optionally substituted by an alkyl of 1 to 6 carbon atoms, n is an integer from 1 to 6, Y is —$(CH_2)_n$— or

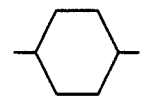

and their non-toxic, pharmaceutically acceptable acid addition salts having remarkable anti-oedematous and anti-inflammatory activity.

12 Claims, No Drawings

ALKYLAMINOAMIDE COMPOUNDS

PRIOR APPLICATION

This application is a division of U.S. patent application Ser. No. 883,914 filed July 10, 1986, now U.S. Pat. No. 4,782,075.

OBJECTS OF THE INVENTION

It is an object of the invention to provide the novel compounds of formula I and their non-toxic, pharmaceutically acceptable addition salts and a process and intermediates for their preparations.

It is another object of the invention to provide novel antiedematous and anti-inflammatory compositions and a method of relieving edemas and inflammation in warm-blooded animals.

These and other objects and advantages of the invention will become obvious from the following detailed description.

THE INVENTION

The novel compounds of the invention are selected from the group consisting of alkylaminoamides of the formula

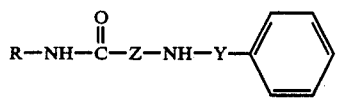
I wherein R is selected from the group consisting of (a) alkyl of 1 to 8 carbon atoms, (b) cycloalkyl of 3 to 7 carbon atoms optionally substituted with phenyl, (c) aryl of 6 to 14 carbon atoms optionally substituted with at least one member of the group consisting of halogen, —CH$_3$, alkyl 1 to 6 carbon atoms, —NO$_2$ and cycloalkyl of 3 to 7 carbon atoms, (d) aralkyl of 7 to 14 carbon atoms and (e)

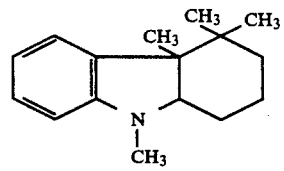

Z is —(CH$_2$)$_n$— optionally substituted by an alkyl of 1 to 6 carbon atoms, n is an integer from 1 to 6, Y is —(CH$_2$)$_n$— or

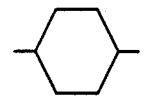

and their non-toxic, pharmaceutically acceptable acid addition salts.

Examples of alkyls of 1 to 8 carbon atoms are methyl, ethyl, n-propyl, isopropyl and linear and branched butyl, hexyl, pentyl, heptyl and octyl and examples of cycloalkyls of 3 to 7 carbon atoms are cyclopropyl, cyclobutyl, cyclopentyl, cyclohexyl and cycloheptyl.

Examples of aryl of 6 to 14 carbon atoms are phenyl and naphthyl, both optionally substituted with at least one member of the group consisting of fluorine, chlorine, bromine, —CF$_3$, —NO$_2$, alkyl of 1 to 6 carbon atoms and cycloalkyl of 3 to 7 carbon atoms. Examples of aralkyl of 7 to 14 carbon atoms are benzyl, phenethyl, phenylpropyl, phenylbutyl, phenylpentyl and phenylhexyl.

Examples of suitable acids for the formation of non-toxic, pharmaceutically acceptable acid addition salts are inorganic acids such as hydrochloric acid, hydrobromic acid, sulfuric acid, nitric acid and phosphoric acid and organic acids such as fumaric acid, acetic acid, propionic acid, glyoxylic acid, fumaric acid, oxalic acid, aspartic acid, alkylsulfonic acids such as methane sulfonic acid and ethane sulfonic acid, aryl sulfonic acids such as benzene sulfonic acid and p-toluene sulfonic acid and aryl carboxylic acids such as benzoic acid.

Among the preferred compounds of formula I are those wherein R is (1,2,3,4,4a,9a-hexahydro-4,4,4a,9-tetramethylcarbazol-2α-yl), (1,2,3,4,4a,9a-hexahydro-4,4,4a,9-tetramethylcarbazol-2β-yl), n-hexyl, cyclohexyl, phenylcyclohexyl or phenyl, or a phenyl substituted by one or two substituents selected from chlorine, cyclohexyl, trifluoromethyl and nitro groups; those wherein Z is —CH$_2$—, —(CH$_2$)$_2$— or —(CH$_2$)$_3$— and those wherein Y is

—(CH$_2$)$_3$— or —(CH$_2$)$_4$— and their non-toxic, pharmaceutically acceptable acid addition salts.

Particularly preferred are compounds of formula I wherein R is (1,2,3,4a,9a-hexahydro-4,4,4a,9-tetramethylcarbazol-2α-yl), (1,2,3,4,4a,9a-hexahydro-4,4,4a,9-tetramethylcarbazol-2β-yl) or substituted phenyl; Z is —(CH$_2$)$_2$— and
Y is trans-

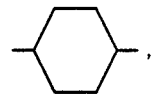

or —(CH$_2$)$_4$— and their acid addition salts thereof.

Among specific preferred compounds of the invention are
N-(1,2,3,4,4a,9a-hexahydro-4,4,4a,9-tetramethylcarbazol-2β-yl)-3-(trans-4-phenylcyclohexylamino)-propionamide;
N-(1,2,3,4,4a,9a-hexahydro-4,4,4a,9-tetramethylcarbazol-2β-yl)-2-(trans-4-phenylcyclohexylamino)-acetamide;
N-(1,2,3,4,4a,9a-hexahydro-4,4,4a,9-tetramethylcarbazol-2α-yl)-3-(4-phenylbutylamino)-propionamide;
N-(1,2,3,4,4a,9a-hexahydro-4,4,4a,9-tetramethyl-carbazol-2β-yl)-3-(3-phenylpropylamino)-propionamide;
N-(1,2,3,4,4a,9a-hexahydro-4,4,4a,9-tetramethylcarbazol-2α-yl)-2-(4-phenylbutylamino)-acetamide;
N-cyclohexyl-3-(trans-4-phenylcyclohexylamino)-propionamide;
N-phenyl-3-(trans-4-phenylcyclohexylamino)-propionamide;
N-n-hexyl-3-(trans-4-phenylcyclohexylamino)-propionamide; and N-(4-chlorophenyl)-3-(trans-4-phenylcyclohex-
ylamino)-propionamide, and their non-toxic, pharma-
ceutically acceptable acid addition salts.

The novel process of the invention for the prepara-
tion of the compounds of formula I comprises reacting
a compound of the formula

   IV wherein R and Z have the above definitions and Hal is
chlorine or bromine with a compound of the formula

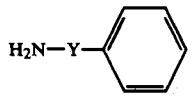   V wherein Y has the above definitions. The reaction is
conveniently carried out in the presence of an organic
solvent such as for example, an aromatic solvent like
benzene or toluene.

The starting compounds of formula IV may be pre-
pared by reacting an amine of the formula

   II wherein R has the above definition with a compound of
the formula

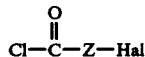   III wherein Z and Hal have the above definitions in the
presence of an acid binding agent such as potassium
carbonate. The reaction may be effected in an organic
solvent such as dichloromethane.

The compounds of formula I are basic in character
and may subsqeuently, if desired, be converted into the
acid addition salts thereof, particularly the physiologi-
cally acceptable acid addition salts thereof with inor-
ganic or organic acids by conventional methods such as
by reacting the compounds as bases with a solution of a
stoichiometric amount of the corresponding acid in a
suitable solvent. Such salts may be prepared in situ in
the reaction mixture without the necessity for interme-
diate isolation of the free bases themselves. Conversely
the acid addition salts of the compounds of formula I
obtained may, if desired, subsequently be converted into
compounds of formula I or into further acid addition
salts thereof.

Of the compounds of formula II, 2-amino-1,2,3,4,4a,-
9a-hexahydro-4,4,4a,9-tetramethylcarbazole is new and
constitutes a further object of the present invention. It
may be prepared by the action of sodium cyanoborohy-
dride on 3,4,4a,9a-tetrahydro-4,4,4a,9-tetramethylcar-
bazol-2-(1H)-one in the presence of a source of ammo-
nia such as ammonium acetate.

The novel antiedematous and anti-inflammatory
compositions of the invention are comprised of an anti-
edematously and anti-inflammatorily effective amount
of at least one compound of formula I and their non-
toxic, pharmaceutically acceptable acid addition salts
and an inert pharmaceutical carrier or excipient. The
compositions may be in the form of tablets, dragees,
capsules, granules, ampoules, suppositories and injecta-
ble solutions or suspensions.

Examples of suitable excipients are talc, gum arabic,
lactose, starch, magnesium stearate, cocoa butter, aque-
ous or non-aqueous vehicles, animal or vegetable fats,
paraffin derivatives, glycols, various wetting, dispersing
or emulsifying agents and/or preservatives.

The compositions possess remarkable antiedematous
and anti-inflammatory activity and are thereof useful
for the treatment of inflammatory diseases.

The novel method of the invention for treating edema
and inflammation in warm-blooded animals, including
humans, comprises administering to warm-blooded ani-
mals an antiedematously and anti-inflammatorily effec-
tive amount of at least one compound of formula I and
their non-toxic, pharmaceutically acceptable acid addi-
tion salts. The active compounds may be administered
orally, rectally, or parenterally. The usual daily dose is
0,001 to 1,4 mg/kg depending on the specific com-
pound, the method of administration and the condition
treated.

In the following examples there are described several
preferred embodiments to illustrate the invention. How-
ever, it is to be understood that the invention is not
intended to be limited to the specific embodiments.

EXAMPLE 1

N-(1,2,3,4,4a,9a-hexahydro-4,4,4a,9-tetramethylcar-
bazol-2$\beta$-yl)-3-(trans-4-phenylcyclohexylamino)-pro-
pionamide and its hydrochloride STEP A: 2-amino-1,2,3,4,4a,9a-hexahydro-4,4,4a,9-
tetramethyl carbazole A mixture of 22 g of 3,4,4a,9a-tetrahydro-4,4,4a,9-tet-
ramethylcarbazol-2-(1H)-one prepared as in J. Chem.
Soc., 1955, 4369, 37 g of ammonium acetate and 4 g of
sodium cyanoborohydride in 300 ml of methanol was
stirred overnight at room temperature under nitrogen.
The mixture was concentrated to 70 ml, diluted with
600 ml of water, acidified to pH of 1 with concentrated
HCl and stirred at room temperature for 1 hour. The
mixture was extracted with ether, adjusted to a pH of 5
with concentrated ammonia, further extracted with
ether and then adjusted to a pH of 10 with concentrated
ammonia. Extraction with ether then gave 11 g of a
50% mixture of $\alpha$- and $\beta$-2-amino-1,2,3,4,4a,9a-hexahy-
dro-4,4,4a,9-tetramethylcarbazole as a pale yellow oil.

STEP B: N-(1,2,3,4,4a,9a-hexahydro-4,4,4a,9-tet-
ramethylcarbazol-2$\beta$-yl)-3-chloropropionamide A mixture of 24.4 g of 2-amino-1,2,3,4,4a,9a-hexahy-
dro-4,4,4a,9-tetramethylcarbazole and 25 g of potassium
carbonate was stirred in 300 ml of dichloromethane
while 14 g of 3-chloropropionyl chloride are added
dropwise. The mixture was stirred overnight at room
temperature and poured into water. The organic layer
was washed with 2N hydrochloric acid and aqueous
sodium bicarbonate, dried over MgSO$_4$ and evaporated
to dryness to give a colorless solid. The solid was sub-
jected to HPLC on "Lichoprep" in dichloromethane to
yield first 6 g (18%) of N-(1,2,3,4,4a,9a-hexahydro-
4,4,4a,9-tetramethylcarbazol-2$\beta$-yl)-3-chloropropiona-
mide melting at 168°-70° C., $\mu_{max}$ 3260 and 1630 cm$^{-1}$,
and then 12 g (36%) of N-(1,2,3,4,4a,9a-hexahydro-
4,4,4a,9-tetramethylcarbazol-2$\beta$-yl)-3-chloropro-
pionamide melting at 166°-8° C., $\nu_{max}$ 3215 and 1630
cm$^{-1}$ STEP C: N-(1,2,3,4,4a,9a-hexahydro-4,4,4a,9-tet-
ramethylcarbazol-2$\beta$-yl)-3-(trans-4-phenylcyclohex-
ylamino)-propionamide 1.5 g of N-(1,2,3,4,4a,9a-hexahydro-4,4,4a,9-tetrame-
thylcarbazol-2$\beta$-yl)-3-chloropropionamide and 3 g of
trans-4-phenylcyclohexylamine prepared as in J. Org.

Chem. (1952) 17, 1017 were stirred under reflux in dry toluene for 3 days. The cooled reaction mixture was filtered and evaporated to dryness under reduced pressure. The residue was chromatographed on silica and elution with dichloromethane-methanol (95:5) gave 1.36g (66%) of N-(1,2,3,4,4a,9a-hexahydro-4,4,4a,9-tetramethylcarbazol-2β-yl)-3-(trans-4-phenylcyclohexylamino)-propionamide as a colorless oil. The oil was dissolved in methanol and treated with ethereal hydrogen chloride to give the colorless, hygroscopic, crystalline hydrochloride salt melting at 184°-6° C. $v_{max}$. 3410, 3265, 1680 cm$^{-1}$.

EXAMPLES 2 TO 20

Using the process of Example 1 but starting from the appropriate amines of formulae II and V and acid chlorides of formula III, the following compounds were prepared:

EXAMPLE 2

N-(1,2,3,4,4a,9a-hexahydro-4,4,4a,9-tetramethylcarbazol-2α-yl)-3-(trans-4-phenylcyclohexylamino)-propionamide.

EXAMPLE 3

N-(1,2,3,4,4a,9a-hexahydro-4,4,4a,9-tetramethylcarbazol-2β-yl)2-(trans-4-phenylcyclohexylamino)-acetamide.

EXAMPLE 4

N-(1,2,3,4,4a,9a-hexahydro-4,4,4a,9-tetramethylcarbazol-2α-yl)-2-(trans-4-phenylcyclohexylamino)-acetamide.

EXAMPLE 5

N-(1,2,3,4,4a,9a-hexahydro-4,4,4a,9-tetramethylcarbazol-2β-yl)-3-(4-phenylbutylamino)-propionamide.

EXAMPLE 6

N-(1,2,3,4,4a,9a-hexahydro-4,4,4a,9-tetramethylcarbazol-2α-yl)-3-(4-phenylbutylamino)-propionamide.

EXAMPLE 7

N-(1,2,3,4,4a,9a-hexahydro)-4,4,4a,9-tetramethylcarbazol-2β-yl)-3-(3-phenylpropylamino)-propionamide.

EXAMPLE 8

N-(1,2,3,4,4a,9a-hexahydro-4,4,4a,9-tetramethylcarbazol-2α-yl)-3-(3-phenylpropylamino)-propionamide.

EXAMPLE 9

N-(1,2,3,4,4a,9a-hexahydro-4,4,4a,9-tetramethylcarbazol-2β-yl)-2-(4-phenylbutylamino)-acetamide.

EXAMPLE 10

N-(1,2,3,4,4a,9a-hexahydro-4,4,4a,9-tetramethylcarbazol-2αyl)-2-(4phenylbutylamino)-acetamide.

EXAMPLE 11

N-cyclohexyl-3-(trans-4-phenylcyclohexylamino)-propionamide.

EXAMPLE 12

N-phenyl-3-(trans-4-phenylcyclohexylamino)-propionamide.

EXAMPLE 13

N-n-hexyl-3-(trans-4-phenylcyclohexylamino)-propionamide.

EXAMPLE 14

N-(4-chlorophenyl)-3-(trans-4-phenylcyclohexylamino)-propionamide.

EXAMPLE 15

N-(4-cyclohexylphenyl)-3-(trans-4-phenylcyclohexylamino)-propionamide.

EXAMPLE 16

N-(3,4-dichlorophenyl)-3-(trans-4-phenylcyclohexylamino)-propionamide.

EXAMPLE 17

N-(4-phenylcyclohexyl)-3-(trans-4-phenylcyclohexylamino)-propionamide.

EXAMPLE 18

N-(3-trifluoromethyl-4-chlorophenyl)-3-(trans-4-phenylcyclohexylamino)-propionamide.

EXAMPLE 19

N-(4-chlorophenyl)-4-trans-4-phenylcyclohexylamino)-butyramide

EXAMPLE 20

N-(3-trifluoromethyl-4-nitrophenyl)-3-(trans-4-phenylcyclohexylamino)-propionamide.

The properties of the said products are reported in the following Table.

TABLE I

RNHCO—Z—NH—Y—⌬

| Ex | R | Z | Y | % | IR(KBr)cm$^{-1}$ | MP |
|----|---|---|---|---|------------------|-----|
| 1  | β | [carbazole structure with CH3, CH3, CH3, N-CH3] | (CH$_2$)$_2$ | trans | 66 | 3410, 3265, 1680, 1660 | 184–6° |
| 2  | α | " | " | " | 85 | 3390, 1650, 1600 | glass |
| 3  | β | " | CH$_2$ | " | 98 | 3400, 3300, 1655, 1600 | 155–6° |
| 4  | α | " | " | " | 70 | 3300, 1650 | glass |
| 5  | β | " | (CH$_2$)$_2$ | (CH$_2$)$_4$ | 60 | 3400, 3220, 1650 | glass |
| 6  | α | " | " | " | 75 | 3280, 1640, 1600 | glass |

TABLE I-continued

RNHCO—Z—NH—Y—⟨phenyl⟩

| Ex | | R | Z | Y | % | IR | mp |
|---|---|---|---|---|---|---|---|
| 7 | β | " | " | $(CH_2)_3$ | 64 | 3400, 3250, 1650 | glass |
| 8 | α | " | " | " | 46 | 3280, 1640, 1600 | glass |
| 9 | β | " | $CH_2$ | $(CH_2)_4$ | 54 | 3300, 1650, 1600 | glass |
| 10 | α | " | " | " | 59 | 3320, 1660, 1640, 1600 | glass |
| 11 | |  cyclohexyl | $(CH_2)_2$ | 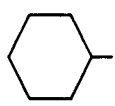 trans-cyclohexyl | 27 | 3340, 1640 | 220° (dec) |
| 12 | | 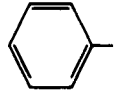 phenyl | " | " | 84 | 3323, 3000–2300, 1665 | 195° (dec) |
| 13 | | $CH_3(CH_2)_5$ | " | " | 27 | 3300, 1640 | 180° (dec) |
| 14 | |  4-Cl-phenyl | " | " | 38 | 3240, 3200, 3160, 3100–2300, 1680, 1665 | 220° (dec) |
| 15 | |  cyclohexylphenyl | " | " | 40 | 3320, 1665 | 265° (dec) |
| 16 | | 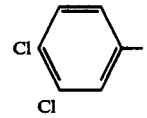 dichlorophenyl | " | " | 49 | 3235, 3160, 1680 | 211–3° |
| 17 | | 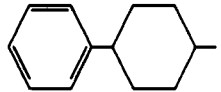 phenylcyclohexyl | " | " | 30 | 3340, 1637 | 262–4 (dec) |
| 18 | | 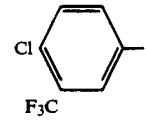 Cl, $F_3C$-phenyl | " | " | 50 | 1686, 1600 | 210–3° |
| 19 | | 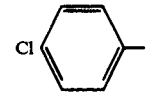 Cl-phenyl | $(CH_2)_3$ | " | 6 | 3320, 1655 | 270° (dec) |
| 20 | |  $O_2N$, $F_3C$-phenyl | $(CH_2)_2$ | " | 52 | 2920, 1690 | 268–70° |

| Ex | Formula | MW | Theory/Found C | H | N | Cl |
|---|---|---|---|---|---|---|
| 1 | | | | | | |
| 2 | $C_{31}H_{43}N_3O \cdot \frac{1}{2}H_2O$ | 482.7 | 77.13 | 9.19 | 8.70 | |
| | | | 77.43 | 9.09 | 8.70 | |
| 3 | $C_{30}H_{41}N_3O \cdot 2HCl$ | 532.6 | 67.66 | 8.14 | 7.89 | |
| | | | 67.93 | 8.12 | 7.85 | |
| 4 | $C_{30}H_{41}N_3O$ | 459.7 | 78.39 | 8.99 | 9.14 | |
| | | | 77.91 | 9.00 | 9.06 | |
| 5 | $C_{29}H_{41}N_3O$ | 447.7 | 76.94 | 9.15 | 9.17 | Theory + 1.3% $CH_2Cl_2$ |
| | | | 76.98 | 9.14 | 9.26 | |
| 6 | $C_{29}H_{41}N_3O$ | 447.7 | 76.89 | 9.14 | 9.08 | Theory + 1.4% |

TABLE I-continued

RNHCO—Z—NH—Y—⟨phenyl⟩

| | | | | | | | |
|---|---|---|---|---|---|---|---|
| | | | 76.92 | 9.13 | 9.25 | | $CH_2Cl_2$ |
| 7 | $C_{28}H_{39}N_5O$ | 433.6 | | | | | |
| 8 | $C_{28}H_{39}N_3O$ | 433.6 | | | | | |
| 9 | $C_{28}H_{39}N_3O$ | 433.6 | 77.16 | 9.12 | 9.58 | | Theory + 0.6% |
| | | | 77.27 | 9.03 | 9.63 | | $CH_2Cl_2$ |
| 10 | $C_{28}H_{39}N_3O$ | 433.6 | 76.08 | 8.87 | 9.47 | | Theory + 2.0% |
| | | | 76.36 | 8.89 | 9.50 | | $CH_2Cl_2$ |
| 11 | $C_{21}H_{32}N_2O \cdot HCl$ | 365.0 | 69.11 | 9.11 | 7.68 | 9.71 | |
| | | | 69.18 | 9.02 | 7.45 | 9.63 | |
| 12 | $C_{21}H_{26}N_2O \cdot HCl$ | 358.9 | 70.28 | 7.58 | 7.80 | 9.88 | |
| | | | 70.36 | 7.54 | 7.62 | 9.87 | |
| 13 | $C_{21}H_{34}N_2O \cdot HCl$ | 367.0 | 68.73 | 9.61 | 7.63 | 9.66 | |
| | | | 68.84 | 9.53 | 7.63 | 9.75 | |
| 14 | $C_{21}H_{25}N_2OCl \cdot HCl$ | 393.4 | 64.12 | 6.66 | 7.12 | 18.03 | |
| | | | 64.05 | 6.66 | 7.13 | 18.00 | |
| 15 | $C_{27}H_{36}N_2O \cdot HCl$ | 441.1 | 73.53 | 8.46 | 6.35 | 8.04 | |
| | | | 73.55 | 8.44 | 6.33 | 8.18 | |
| 16 | $C_{21}H_{24}N_2OCl_2 \cdot HCl$ | 427.8 | 58.96 | 5.89 | 6.55 | 24.86 | |
| | | | 59.15 | 5.91 | 6.37 | 24.74 | |
| 17 | $C_{27}H_{36}N_2O \cdot HCl$ | 441.1 | 73.53 | 8.46 | 6.35 | 8.04 | |
| | | | 73.42 | 8.40 | 6.31 | 8.11 | |
| 18 | $C_{22}H_{25}N_2OF_3Cl_2$ | 461.4 | 57.28 | 5.46 | 6.07 | | 12.35(F) |
| | | | 57.36 | 5.50 | 5.99 | | 12.26 |
| 19 | $C_{22}H_{25}N_2OCl \cdot HCl$ | 407.4 | 64.86 | 6.93 | 6.88 | 17.41 | |
| | | | 64.91 | 6.93 | 6.86 | 17.41 | |
| 20 | $C_{22}H_{24}N_3O_3F_3$ | 435.5 | 60.68 | 5.56 | 9.65 | | 13.09(F) |
| | | | 60.55 | 5.60 | 9.58 | | 13.04 |

NOTE: Analysis of salts of the carbazole amides was difficult due to hygroscopicity and analysis of their free bases was complicated by their non-crystalline nature and consequential occlusion of dichloromethane.

EXAMPLE 21

Tablets were prepared containing 20 mg of the compound of Example 1 or 6 and sufficient excipient of lactose, starch, talc and magnesium stearate for a final weight of 150 mg.

PHARMACOLOGICAL DATA

The anti-oedematous properties of the compounds were assessed by utilization of a modification of the carrageenin-induced oedema procedure [Proc. Soc. Exp. Biol. Med., 1962, Vol. 11, 544] following administration to male Wistar rats. The data in the following Table display the percentage inhibition by weight compared to control after a dose of 100 mg/kg p.o. or 50 mg/kg i.p.

| Example | Inhibition | |
|---|---|---|
| 1 | 87.7 | (i.p.), 14.1 (p.o.) |
| 2 | 82.3 | (i.p.), 34.8 (p.o.) |
| 3 | 57.4 | (i.p.), 12.9 (p.o.) |
| 5 | 36.4 | (p.o.) |
| 6 | 43.6 | (p.o.) |
| 7 | 16.5 | (p.o.) |
| 8 | 40.8 | (p.o.) |
| 9 | 28.7 | (p.o.) |
| 10 | 15.1 | (p.o.) |
| 11 | 18 | (p.o.) |
| 12 | 13 | (p.o.) |
| 13 | 17 | (p.o.) |
| 14 | 15 | (p.o.) |
| 15 | 26 | (p.o.) |
| 16 | 19 | (p.o.) |
| 17 | 28 | (p.o.) |
| 18 | 25 | (p.o.) |
| 19 | 24.8 | (p.o.) |

| -continued | | |
|---|---|---|
| Example | Inhibition | |
| 20 | 5.8 | (p.o.) |

Various modifications of the products and process of the invention may be made without departing from the spirit or scope thereof and it is to be understood that the invention is intended to be limited only as defined in the appended claims.

What we claim is:

1. A compound selected from the group consisting of alkylaminoamides of the formula

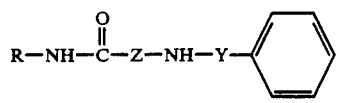

wherein R is selected from the group consisting of (a) alkyl of 1 to 8 carbon atoms, (b) cycloalkyl of 3 to 7 carbon atoms unsubstituted or substituted with phenyl, (c) aryl of 6 to 14 carbon atoms unsubstituted or substituted with at least one member of the group consisting of halogen, —$CF_3$, alkyl of 1 to 6 carbon atoms, —$NO_2$ and cyclohexyl (d) aralkyl of 7 to 14 carbon atoms and (e)

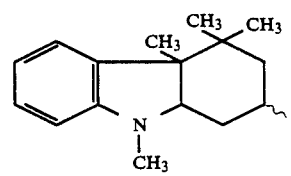

Z is linear or branched alkyl of 1 to 12 carbon atoms Y is —$(CH_2)_n$— or

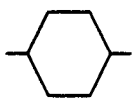

and their non-toxic, pharmaceutically acceptable acid addition salts.

2. A compound of claim 1 wherein R is selected from the group consisting of n-hexyl, cyclohexyl, phenylcyclohexyl, phenyl and phenyl substituted by one or two substituents selected from the group consisting of chlorine, cyclohexyl, trifluoromethyl and nitro; Z is selected from the group consisting of —CH$_2$—, —(CH$_2$)$_2$— and —(CH$_2$)$_3$— and Y is selected from the group consisting of

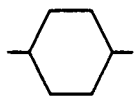

—(CH$_2$)$_3$— and —(CH$_2$)$_4$—.

3. A compound of claim 1 wherein R is substituted phenyl, Z is selected from the group consisting of —(CH$_2$)$_2$— and Y is selected from the group consisting of

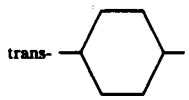

or —(CH$_2$)$_4$—.

4. A compound of claim 1 selected from the group consisting of N-(cyclohexyl-3-(trans-4-phenylcyclohexylamino)-propionamide; N-phenyl-3-(trans-4-phenylcyclohexylamno)-propionamide; N-n-hexyl-3-(trans-4-phenyl cyclohexylamino)-propionamide; and N-(4-chlorophenyl)-3-(trans-4-phenylcyclohexylamino)-propionamide and their non-toxic, pharmaceutically acceptable acid additions salts.

5. An antiedematous and anti-inflammatory composition comprising an antiedematously and anti-inflammatorily effective amount of at least one compound of claim 1, and an excipient.

6. A composition of claim 5 wherein R is selected from the group consisting of n-hexyl, cyclohexyl, phenylcyclohexyl, phenyl and phenyl substituted by one of two substituents selected from the group consisting of chlorine, cyclohexyl, trifluoromethyl and nitro; Z is selected from the group consisting of —CH$_2$—, —(CH$_2$)$_2$— and (CH$_2$)$_3$— Y is selected from the group consisting of

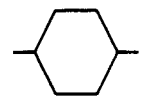

—(CH$_2$)$_3$— and —(CH$_2$)$_4$—.

7. A composition of claim 5 wherein R is substituted phenyl; Z is selected from the group consisting of —(CH$_2$)$_2$— and Y is selected from the group consisting of

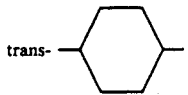

or —(CH$_2$0$_4$—.

8. A composition of claim 5 wherein the active compound is selected from the group consisting of N-cyclohexyl-3-(trans-4-phenylcyclohexylamino)-propionamide; N-phenyl-3-(trans-4-phenylcyclohexylamino)propionamide; N-n-hexyl-3-(trans-4-phenylcyclohexylamino)-propionamide; and N-(4-chlorophenyl)-3-(trans-4-phenylcyclohexylamino-propionamide and their non-toxic, pharmaceutically acceptable acid addition salts.

9. A method of treating edema and inflammation in warm-blooded animals comprises administering to warm-blooded animals an antiedematously and antiinflammatorily effective mount of at least one compound of claim 1.

10. A method of claim 9 wherein R is selected from the group consisting of n-hexyl, cyclohexyl, phenylcyclohexyl, phenyl and phenyl substituted by one or two substituents selected from the group consisting of chlorine, cyclohexyl, trifluoromethyl and nitro; Z is selected from the group consisting of —CH$_2$—, —(CH$_2$)$_2$— and —(CH$_2$)$_3$— and Y is selected from the group consisting of

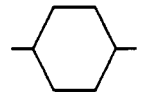

—(CH$_2$)$_3$— and (CH$_2$)$_4$—.

11. A method of claim 9 wherein R is substituted phenyl; Z is selected from the group consisting of —(CH$_2$)$_2$— and Y is selected from the group consisting of

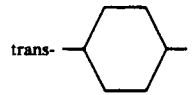

or —(CH$_2$)$_4$—.

12. A method of claim 9 wherein the compound is selected from the group consisting of N-cyclohexyl-3-(trans-4-phenylcyclohexylamino)-propionamide; N-phenyl-3-(trans-4-phenylcyclohexylamino)-propionamide; N-n-hexyl-3-(trans-4-phenylcyclohexylamino)-propionamide; and N-(4-chlorophenyl)-3-(trans-4-phenylcyclohexylamino)-propionamide and their nontoxic, pharmaceutically acceptable acid addition salts.

* * * * *